United States Patent [19]

Barre et al.

[11] Patent Number: 5,587,304
[45] Date of Patent: Dec. 24, 1996

[54] **CLONING AND EXPRESSION OF THE GENE OF THE MALOLACTIC ENZYME OF *LACTOCOCCUS LACTIS***

[75] Inventors: Pierre Barre, Saint Gely du Fesc; Sylvie Dequin; Virginie Ansanay, both of Montpellier, all of France

[73] Assignee: Institut National de la Recherche Agronomique - I.N.R.A., Paris Cedex, France

[21] Appl. No.: 367,227
[22] PCT Filed: May 18, 1994
[86] PCT No.: PCT/FR94/00589
    § 371 Date: Jan. 17, 1995
    § 102(e) Date: Jan. 17, 1995
[87] PCT Pub. No.: WO94/26879
    PCT Pub. Date: Nov. 24, 1994

[30] Foreign Application Priority Data

May 18, 1993 [FR] France ................... 93 06003

[51] Int. Cl.$^6$ .............. C12P 7/50; C12N 15/53; C12N 15/70; C12N 15/81
[52] U.S. Cl. ............... 435/139; 435/320.1; 435/252.33; 435/254.2; 435/254.21; 435/189; 536/232
[58] Field of Search ................. 435/139, 320.1, 435/252.33, 254.21, 189, 254.2; 536/23.2

[56] References Cited

FOREIGN PATENT DOCUMENTS 0103339  3/1984  European Pat. Off. .

OTHER PUBLICATIONS

Ansanay, V., et al. (1993) FEBS Letts. 332 (1,2), 74–80.
Danayrolles, M., et al. (1994) FEMS Microbiol. Letts. 116, 79–86.
Renault, P., et al. (1990) Biotech. Abs. 92–03363.
Renault, P., et al. (1987) Biosis Previews Database, 83085283.

*Primary Examiner*—Charles L. Patterson, Jr.
*Attorney, Agent, or Firm*—Oblon, Spivak, McClelland, Maier & Neustadt, P.C.

[57] ABSTRACT

An isolated nucleic acid fragment comprising a sequence of 1620 bp encoding the malolactic enzyme of *Lactococcus lactis*.

15 Claims, 3 Drawing Sheets

```
Seq L. lactis   5'      ATGGTGCACATGA              3' primer 1        5'  GGCTCGAGATGGTGCACATGA          3'
                        XhoI primer 12       5'  TCGGATCCATGGTGCACATGA          3'
                        BamHI Seq L. lactis   5'  GAGTACTAAGGGGAATATCT           3' primer 3                  3'  ATGATTCCCCTTATAGATCTGT    5'
                                              XbaI primer 13       3'  CTCATGATTCCCCTCGAGTC           5'
                                    SacI
```

FIG. 2

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 2684 base pairs
        ( B ) TYPE: nucleic acid
        ( C ) STRANDEDNESS: single
        ( D ) TOPOLOGY: linear ( i i ) MOLECULE TYPE: DNA (genomic)

( i v ) ANTI-SENSE: NO ( i x ) FEATURE:
        ( A ) NAME/KEY: CDS
        ( B ) LOCATION: 466..2085

( i x ) FEATURE:
        ( A ) NAME/KEY: -35_signal
        ( B ) LOCATION: 392..397

( i x ) FEATURE:
        ( A ) NAME/KEY: -10_signal
        ( B ) LOCATION: 416..421

( x i ) SEQUENCE DESCRIPTION: SEQ ID NO:1:

```
TTTGTTGAA  AAAATTTCTA  ATCAAATTAT  TAACCTAAAA  GATACATAAA  TTTAAAAAAT       60

AAAAGTAGAG  TGATTTTACT  CTACTTTTTT  AGAATACTTT  TATATAATAG  GAAATATGAA      120

TAAAGCAAAG  CGCACAATTT  TGGTTTTATT  TAAAAAAATG  GATACCTTAG  ATACACAACC      180

ACCATTGACA  AAAAATCTTA  ATCCTAAATT  GGTTGAAACC  CTGATAAATT  AGGGATAGTA      240

ATAGGAGGAG  GACAGTTTAT  CATTTAATAG  TTATAAGCTA  ATTTTACTA   CCATTTCTTT      300

GATTAATATC  ATCTATTTTT  ATATAGAGAC  TTTTAAATAA  ACATTGACAT  TATTTATGCG      360

TTATAAATTA  AATTTATCAA  CACTAAGGAA  TTTGACTATA  ACGATAAAAG  AAGTTTATAG      420

TAATAAAGTA  ATAACATTAA  TTATAATTTT  AATGGAGGTT  GTACG ATG CGT GCA           474
                                                    Met Arg Ala
                                                     1

CAT GAA ATT TTA AAC AAT CCT TTT TTA AAT AAA GGA ACA GCT TTT ACT            522
His Glu Ile Leu Asn Asn Pro Phe Leu Asn Lys Gly Thr Ala Phe Thr
     5               10              15

ATG AAA GAC CGT CAA GAA TTG GGG TTG ATT GGT CTT CTT CCA CCA ACT            570
Met Lys Asp Arg Gln Glu Leu Gly Leu Ile Gly Leu Leu Pro Pro Thr
 20              25              30                           35

GTT CAA ACA ATT GAG GAA CAA GCT GAA CAA ACT TAC GAA CAA TAT TTG            618
Val Gln Thr Ile Glu Glu Gln Ala Glu Gln Thr Tyr Glu Gln Tyr Leu
                 40              45                      50

ACA AAA CCA TCT GAT TTA GAA AAA CGT CAT TTC TTG ATG GAA ATT TTT            666
Thr Lys Pro Ser Asp Leu Glu Lys Arg His Phe Leu Met Glu Ile Phe
             55              60              65

AAT ACA AAC CGT ACT TTG TTT TAC TAC TTA TTC AAC AAA CAT ATT GTA            714
Asn Thr Asn Arg Thr Leu Phe Tyr Tyr Leu Phe Asn Lys His Ile Val
         70              75              80

GAA TTT AAT CCA GTT GTT TAT GAT CCA ACA ATT GCT GAT ACA ATT GAA            762
Glu Phe Asn Pro Val Val Tyr Asp Pro Thr Ile Ala Asp Thr Ile Glu
     85              90              95

AAC TAC AGT CAT TTG TTC GTA GAT CCA CAA TAT GCT GCT TAT CTT GAT            810
Asn Tyr Ser His Leu Phe Val Asp Pro Gln Tyr Ala Ala Tyr Leu Asp
100             105             110                     115
```

| | | | | | | | | | | | | | | | | |
|---|---|---|---|---|---|---|---|---|---|---|---|---|---|---|---|---|
| ATT | AAC | CAC | CCT | GAA | AAC | ATT | ACT | GAA | ACA | TTG | AAA | AGT | GCA | GCA | GGT | 858 |
| Ile | Asn | His | Pro | Glu | Asn | Ile | Thr | Glu | Thr | Leu | Lys | Ser | Ala | Ala | Gly | |
| | | | | 120 | | | | | 125 | | | | | 130 | | |
| GAC | AGA | GAA | ATT | CGT | CCT | ATT | GTT | GTA | ACT | GAT | GCT | GAA | GGA | ACC | CTT | 906 |
| Asp | Arg | Glu | Ile | Arg | Pro | Ile | Val | Val | Thr | Asp | Ala | Glu | Gly | Thr | Leu | |
| | | | 135 | | | | | 140 | | | | | 145 | | | |
| GGT | ATT | GGA | GAC | TGG | GGA | ACT | CAA | GGT | GTT | GAT | ATC | TCA | GTT | GGT | AAA | 954 |
| Gly | Ile | Gly | Asp | Trp | Gly | Thr | Gln | Gly | Val | Asp | Ile | Ser | Val | Gly | Lys | |
| | | 150 | | | | | 155 | | | | | 160 | | | | |
| TTA | ATG | ATT | TAT | ACA | GCC | GCA | GCA | GGT | ATT | GAT | CCA | GCG | TCT | GTA | CTT | 1002 |
| Leu | Met | Ile | Tyr | Thr | Ala | Ala | Ala | Gly | Ile | Asp | Pro | Ala | Ser | Val | Leu | |
| | 165 | | | | | 170 | | | | | 175 | | | | | |
| CCA | GTT | GTT | ATT | GAT | GCA | GGG | ACA | AAT | AGG | AAA | GGA | CTT | TTA | GAA | GAT | 1050 |
| Pro | Val | Val | Ile | Asp | Ala | Gly | Thr | Asn | Arg | Lys | Gly | Leu | Leu | Glu | Asp | |
| 180 | | | | | 185 | | | | | 190 | | | | | 195 | |
| CAT | TTG | TAT | CTT | GGA | AAT | CAT | CAA | GAA | CGT | ATT | TAC | GGT | GAT | CAA | TAC | 1098 |
| His | Leu | Tyr | Leu | Gly | Asn | His | Gln | Glu | Arg | Ile | Tyr | Gly | Asp | Gln | Tyr | |
| | | | | 200 | | | | | 205 | | | | | 210 | | |
| TAC | AGT | TTC | GTC | GAT | CAA | TTT | GTA | GAA | ACT | GCA | GAA | TCA | ATT | TTC | CCT | 1146 |
| Tyr | Ser | Phe | Val | Asp | Gln | Phe | Val | Glu | Thr | Ala | Glu | Ser | Ile | Phe | Pro | |
| | | | 215 | | | | | 220 | | | | | 225 | | | |
| AAA | TTG | TAC | CTT | CAC | TGG | GAA | GAT | TTC | GGA | CGT | TCA | AAT | GCT | GCA | ACA | 1194 |
| Lys | Leu | Tyr | Leu | His | Trp | Glu | Asp | Phe | Gly | Arg | Ser | Asn | Ala | Ala | Thr | |
| | | 230 | | | | | 235 | | | | | 240 | | | | |
| ATT | TTA | AAT | AAC | TAC | AAA | ACA | AAA | ATC | CCA | ACA | TTT | AAT | GAT | GAC | ATT | 1242 |
| Ile | Leu | Asn | Asn | Tyr | Lys | Thr | Lys | Ile | Pro | Thr | Phe | Asn | Asp | Asp | Ile | |
| | 245 | | | | | 250 | | | | | 255 | | | | | |
| CAA | GGA | ACT | GGT | ATT | GTT | GTT | TTA | GGT | GGT | ATT | TTC | GGA | TCA | CTT | GAC | 1290 |
| Gln | Gly | Thr | Gly | Ile | Val | Val | Leu | Gly | Gly | Ile | Phe | Gly | Ser | Leu | Asp | |
| 260 | | | | | 265 | | | | | 270 | | | | | 275 | |
| ATT | ACA | GGT | GAA | AAA | TTA | ACT | GAT | CAA | GTA | TAT | CTT | TGC | TAT | GGT | GGT | 1338 |
| Ile | Thr | Gly | Glu | Lys | Leu | Thr | Asp | Gln | Val | Tyr | Leu | Cys | Tyr | Gly | Gly | |
| | | | | 280 | | | | | 285 | | | | | 290 | | |
| GGT | TCA | GCC | GGT | GCA | GGG | ATT | GCT | GGT | CGT | GTT | CAT | GCT | GAA | ATG | GTT | 1386 |
| Gly | Ser | Ala | Gly | Ala | Gly | Ile | Ala | Gly | Arg | Val | His | Ala | Glu | Met | Val | |
| | | | 295 | | | | | 300 | | | | | 305 | | | |
| AGT | GAA | GGT | CTT | TCT | GAA | GAA | GAA | GCT | TAC | AAA | CAT | TTC | TTC | ATG | ATT | 1434 |
| Ser | Glu | Gly | Leu | Ser | Glu | Glu | Glu | Ala | Tyr | Lys | His | Phe | Phe | Met | Ile | |
| | | 310 | | | | | 315 | | | | | 320 | | | | |
| GAT | CAA | CAA | GGT | TTA | CTT | TTT | GAT | GAT | ATG | GAA | GAC | CTT | ACA | CCA | GCT | 1482 |
| Asp | Gln | Gln | Gly | Leu | Leu | Phe | Asp | Asp | Met | Glu | Asp | Leu | Thr | Pro | Ala | |
| | 325 | | | | | 330 | | | | | 335 | | | | | |
| CAA | AAA | CCA | TTT | GCT | AAA | AAA | CGT | GCT | GAT | TAT | AAA | GAT | GCT | GGA | GAT | 1530 |
| Gln | Lys | Pro | Phe | Ala | Lys | Lys | Arg | Ala | Asp | Tyr | Lys | Asp | Ala | Gly | Asp | |
| 340 | | | | | 345 | | | | | 350 | | | | | 355 | |
| ATG | ACT | GAC | CTT | CTT | AAC | GTT | GTT | AAG | ACA | GTA | AAA | CCA | ACT | ATT | TTA | 1578 |
| Met | Thr | Asp | Leu | Leu | Asn | Val | Val | Lys | Thr | Val | Lys | Pro | Thr | Ile | Leu | |
| | | | | 360 | | | | | 365 | | | | | 370 | | |
| GTA | GGA | ACT | TCA | ACT | AAT | CCA | GGT | GCC | TTT | ACA | AAA | GAA | GTT | GTT | GAA | 1626 |
| Val | Gly | Thr | Ser | Thr | Asn | Pro | Gly | Ala | Phe | Thr | Lys | Glu | Val | Val | Glu | |
| | | | 375 | | | | | 380 | | | | | 385 | | | |
| GCA | ATG | TGT | GCT | AAT | ACA | GAA | CGC | CCA | GTA | ATC | TTC | CCT | ATC | TCA | AAT | 1674 |
| Ala | Met | Cys | Ala | Asn | Thr | Glu | Arg | Pro | Val | Ile | Phe | Pro | Ile | Ser | Asn | |
| | | 390 | | | | | 395 | | | | | 400 | | | | |
| CCA | ACT | AAA | AAA | ATG | GAA | ACT | ACA | GCT | GAA | CAA | GTT | ATT | GAG | TGG | TCT | 1722 |
| Pro | Thr | Lys | Lys | Met | Glu | Thr | Thr | Ala | Glu | Gln | Val | Ile | Glu | Trp | Ser | |
| | 405 | | | | | 410 | | | | | 415 | | | | | |
| GAT | GGA | AAA | GCT | TTT | GTC | GCT | ACT | GGT | GTT | CCT | TCA | GGA | ACA | ATC | AGC | 1770 |
| Asp | Gly | Lys | Ala | Phe | Val | Ala | Thr | Gly | Val | Pro | Ser | Gly | Thr | Ile | Ser | |
| 420 | | | | | 425 | | | | | 430 | | | | | 435 | |

```
TAC AAA GGT GTT GAT TAT CAA ATT GGT CAA GCA AAT AAC TCA CTT ATC       1818
Tyr Lys Gly Val Asp Tyr Gln Ile Gly Gln Ala Asn Asn Ser Leu Ile
            440                 445                 450

CAC CCA GGT TTG GGC TTA GGA ATG TTG GCA TCT GAA GCA AAA CTT TTG       1866
His Pro Gly Leu Gly Leu Gly Met Leu Ala Ser Glu Ala Lys Leu Leu
                455                 460                 465

ACA GAT GAA ATG ATC GGT GCA GCT GCA CAT TCA TTG AGC GGT TTA GTA       1914
Thr Asp Glu Met Ile Gly Ala Ala Ala His Ser Leu Ser Gly Leu Val
            470                 475                 480

GAT CCA GGT AAA CCA GGT GCT CCT GTT CTT CCT CCA TTT GAA TTT GTT       1962
Asp Pro Gly Lys Pro Gly Ala Pro Val Leu Pro Pro Phe Glu Phe Val
        485                 490                 495

GCT GAT GTA TCA ATT AAA GTT GCA GAA GCA GTT GCT AAG AAA GCT CAA       2010
Ala Asp Val Ser Ile Lys Val Ala Glu Ala Val Ala Lys Lys Ala Gln
500                 505                 510                 515

GAA CAA GGT CTT ACT GAA TCT AAA GAA ACT GAT ATG GCT AAA GCA GTT       2058
Glu Gln Gly Leu Thr Glu Ser Lys Glu Thr Asp Met Ala Lys Ala Val
                520                 525                 530

CGT GAT CTT AAA TGG TAT CCA GAG TAC TAAGGGGAAT ATCTTAAATG             2105
Arg Asp Leu Lys Trp Tyr Pro Glu Tyr
            535                 540

AAAAAACTTA AAGAAACGAA AATATCGGGA ATTAGTCTTC CCTTATATGC CTTTTTCGTA     2165

GCTGTCATCA TAGTTGTAAC ACTATTAGGA AAACTTCCAC TTGATATGGT AGGGTTAACT     2225

CTCCTACTTG TAACATTAGG CCACCTATTA TACTTCATAG GAGAAAAATT CCCTATTATG     2285

AATTCATACT TAGGTGGGGG ATCTGTTTTC ACTTAATTG GTGCTACTCT ATTATCTTTC      2345

TTCCACATTG TTCCTTCAAA TGTTATTGGA GCAGTTCCA ATTTATGGG TGGAAAATTT       2405

GGATTTCTTG ATTTTTATAT AGCTGCACTT ATCTGTGGAT CTATTTTAGG AATGAACAGA     2465

AATCTTTTGG TTAAAGCTTC CAAGAAATTT ATTCCGATTG CTTTAATCAC TATGGTTATT     2525

GGTTCTTCT CAGTAGGTCT TGTAGGAATG CTTATTGGTA ATGGATTTGC TGATTCTGTA      2585

ATGTATGTTT CTATGCCAAT GATGTCAGGT GGTATGGGAG CCGGAATTAC TCACTCTCTC    2645

AAATCTATGC AGCCGGATTG GCTCATGGAA ACCAAGCAG                            2684
```

( 2 ) INFORMATION FOR SEQ ID NO:2:

( i ) SEQUENCE CHARACTERISTICS:
        ( A ) LENGTH: 540 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Arg Ala His Glu Ile Leu Asn Asn Pro Phe Leu Asn Lys Gly Thr
 1               5                  10                  15

Ala Phe Thr Met Lys Asp Arg Gln Glu Leu Gly Leu Ile Gly Leu Leu
            20                  25                  30

Pro Pro Thr Val Gln Thr Ile Glu Glu Gln Ala Glu Gln Thr Tyr Glu
        35                  40                  45

Gln Tyr Leu Thr Lys Pro Ser Asp Leu Glu Lys Arg His Phe Leu Met
    50                  55                  60

Glu Ile Phe Asn Thr Asn Arg Thr Leu Phe Tyr Tyr Leu Phe Asn Lys
65                  70                  75                  80

His Ile Val Glu Phe Asn Pro Val Val Tyr Asp Pro Thr Ile Ala Asp
            85                  90                  95

Thr Ile Glu Asn Tyr Ser His Leu Phe Val Asp Pro Gln Tyr Ala Ala
                100                 105                 110
```

```
Tyr  Leu  Asp  Ile  Asn  His  Pro  Glu  Asn  Ile  Thr  Glu  Thr  Leu  Lys  Ser
          115                      120                 125

Ala  Ala  Gly  Asp  Arg  Glu  Ile  Arg  Pro  Ile  Val  Val  Thr  Asp  Ala  Glu
     130                      135                 140

Gly  Thr  Leu  Gly  Ile  Gly  Asp  Trp  Gly  Thr  Gln  Gly  Val  Asp  Ile  Ser
145                      150                      155                      160

Val  Gly  Lys  Leu  Met  Ile  Tyr  Thr  Ala  Ala  Ala  Gly  Ile  Asp  Pro  Ala
               165                      170                      175

Ser  Val  Leu  Pro  Val  Val  Ile  Asp  Ala  Gly  Thr  Asn  Arg  Lys  Gly  Leu
               180                 185                      190

Leu  Glu  Asp  His  Leu  Tyr  Leu  Gly  Asn  His  Gln  Glu  Arg  Ile  Tyr  Gly
          195                 200                      205

Asp  Gln  Tyr  Tyr  Ser  Phe  Val  Asp  Gln  Phe  Val  Glu  Thr  Ala  Glu  Ser
     210                 215                      220

Ile  Phe  Pro  Lys  Leu  Tyr  Leu  His  Trp  Glu  Asp  Phe  Gly  Arg  Ser  Asn
225                      230                 235                           240

Ala  Ala  Thr  Ile  Leu  Asn  Asn  Tyr  Lys  Thr  Lys  Ile  Pro  Thr  Phe  Asn
               245                      250                      255

Asp  Asp  Ile  Gln  Gly  Thr  Gly  Ile  Val  Val  Leu  Gly  Gly  Ile  Phe  Gly
               260                      265                      270

Ser  Leu  Asp  Ile  Thr  Gly  Glu  Lys  Leu  Thr  Asp  Gln  Val  Tyr  Leu  Cys
          275                      280                 285

Tyr  Gly  Gly  Gly  Ser  Ala  Gly  Ala  Gly  Ile  Ala  Gly  Arg  Val  His  Ala
     290                 295                      300

Glu  Met  Val  Ser  Glu  Gly  Leu  Ser  Glu  Glu  Ala  Tyr  Lys  His  Phe
305                      310                      315                      320

Phe  Met  Ile  Asp  Gln  Gln  Gly  Leu  Leu  Phe  Asp  Asp  Met  Glu  Asp  Leu
                    325                 330                      335

Thr  Pro  Ala  Gln  Lys  Pro  Phe  Ala  Lys  Lys  Arg  Ala  Asp  Tyr  Lys  Asp
               340                 345                      350

Ala  Gly  Asp  Met  Thr  Asp  Leu  Leu  Asn  Val  Val  Lys  Thr  Val  Lys  Pro
          355                      360                 365

Thr  Ile  Leu  Val  Gly  Thr  Ser  Thr  Asn  Pro  Gly  Ala  Phe  Thr  Lys  Glu
     370                      375                      380

Val  Val  Glu  Ala  Met  Cys  Ala  Asn  Thr  Glu  Arg  Pro  Val  Ile  Phe  Pro
385                      390                      395                      400

Ile  Ser  Asn  Pro  Thr  Lys  Lys  Met  Glu  Thr  Thr  Ala  Glu  Gln  Val  Ile
               405                      410                      415

Glu  Trp  Ser  Asp  Gly  Lys  Ala  Phe  Val  Ala  Thr  Gly  Val  Pro  Ser  Gly
          420                      425                      430

Thr  Ile  Ser  Tyr  Lys  Gly  Val  Asp  Tyr  Gln  Ile  Gly  Gln  Ala  Asn  Asn
          435                      440                      445

Ser  Leu  Ile  His  Pro  Gly  Leu  Gly  Leu  Gly  Met  Leu  Ala  Ser  Glu  Ala
     450                      455                      460

Lys  Leu  Leu  Thr  Asp  Glu  Met  Ile  Gly  Ala  Ala  Ala  His  Ser  Leu  Ser
465                      470                      475                      480

Gly  Leu  Val  Asp  Pro  Gly  Lys  Pro  Gly  Ala  Pro  Val  Leu  Pro  Pro  Phe
               485                      490                      495

Glu  Phe  Val  Ala  Asp  Val  Ser  Ile  Lys  Val  Ala  Glu  Ala  Val  Ala  Lys
               500                      505                      510

Lys  Ala  Gln  Glu  Gln  Gly  Leu  Thr  Glu  Ser  Lys  Glu  Thr  Asp  Met  Ala
               515                      520                      525

Lys  Ala  Val  Arg  Asp  Leu  Lys  Trp  Tyr  Pro  Glu  Tyr
```

(2) INFORMATION FOR SEQ ID NO:3:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:3:

GGCTCGAGAT GCGTGCACAT GA        22

(2) INFORMATION FOR SEQ ID NO:4:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:4:

TCGGATCCAT GCGTGCACAT GA        22

(2) INFORMATION FOR SEQ ID NO:5:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:5:

ATGATTCCCC TTATAGATCT GT        22

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:6:

CTCATGATTC CCCTCGAGTC        20

(2) INFORMATION FOR SEQ ID NO:7:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO:7:

ATGCGTGCAC ATGA        14

(2) INFORMATION FOR SEQ ID NO:8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:8:

GAGTACTAAG GGGAATATCT        20

(2) INFORMATION FOR SEQ ID NO:9:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:9:

ATGMGNGCNC AYGARAT        17

CLONING AND EXPRESSION OF THE GENE OF THE MALOLACTIC ENZYME OF LACTOCOCCUS LACTIS

The present invention relates to the cloning of the structural gene for the malolactic enzyme of *Lactococcus lactis*, to its complete nucleotide sequence and to the deduced protein sequence, as well as to DNA fragments carrying the sequence encoding this gene. It also relates to the expression of this gene in various prokaryotic or eukaryotic hosts, and in particular in Saccharomyces and Schizosaccharomyces.

Malolactic fermentation, a secondary fermentation which is observed during the process of winemaking in addition to the alcoholic fermentation performed by yeasts, consists in the degradation, by certain lactic acid bacteria, of the malic acid present in wines, to lactic acid and $CO_2$. The bacterial species naturally present in the fermentative flora and which are responsible for the malolactic fermentation belong to the genera Lactobacillus, Leuconostoc and Pediococcus.

This reaction has two main advantages:

It leads to a deacidification of the wine by conversion of a diacid (L-malate) to a monoacid (L-lactate), the consequences of which are advantageous at the organoleptic level, for the majority of red wines and some white wines, It permits the microbiological stabilization of the wine, and therefore a better preservation, by using a fermentable substrate, which prevents subsequent fermentations by other strains of undesirable microorganisms. Finally, malolactic fermentation can have an influence on the quality of the wine from the aromatic point of view.

This reaction poses, however, a certain number of problems because of its slowness and its uncontrollable character.

Malolactic fermentation occurs spontaneously only at the end of the natural wine-making process; indeed, the pH, the ethanol content and the presence of $SO_2$ in the wine considerably slow down the growth of the lactic acid bacteria naturally present in the fermenting mass and which are responsible for the malolactic fermentation. In order to try to accelerate this fermentation, the technique most commonly used lies in the addition, to the fermenting medium, of an inoculum of lactic acid bacteria.

However, this technique does not always resolve the problems of implantation of the lactic acid bacteria because of the difficulty which they have in adapting to the wine medium. Moreover, the introduction of lactic acid bacteria amounts to adding, in addition to the malolactic enzyme whose activity is desired, numerous other enzymes whose action on the numerous substrates present in the wine can result in a development of the organoleptic qualities of the product which is very difficult to control.

It would therefore be desirable to have the possibility of carrying out the malolactic fermentation so as to arrive rapidly, and while removing uncontrollable variables, at an improvement of the product obtained.

With the aim of better controlling the malolactic fermentation, it has been proposed to clone the genes for the malolactic enzymes of lactic acid bacteria, and to introduce and express them in the microorganism which is normally involved in the manufacture of wine, such as *S. Cerevisiae*.

WILLIAMS et al. [App. Environ. Microbiol. 47: 288–293 (1984)], as well as European Application 103300 describe the cloning of a 5 kb DNA fragment carrying the gene for the malolactic enzyme *L. delbrueckii* into *S. Cerevisiae* and into *E. coli*.

The gene for the malolactic enzyme of *L. oenos* has also been cloned into *E. Coli* [LAUTENACH et al., Microbiol., 39:29–39 (1984)].

However, the strains of microorganisms transformed express the gene only at a very low level, insufficient to permit its use in the manufacture of wine.

In addition, in both cases, an instability of the DNA cloned into *E. Coli* was observed, even going as far as bringing about the complete loss of the gene.

Moreover, a malolactic enzyme, having an activity of a level comparable to that of the malolactic enzyme of bacteria of the genera Leuconostoc, Pediococcus and Lactobacillus mentioned above, have recently been purified from *Lactococcus lactis*. It is a protein of about 230 kDa, consisting of subunits of about 56 kDa. Its pHi. is about 4.3, and its Km for malic acid is about 10 to 12 mM. Its N-terminal sequence has also been determined [RENAULT, Malolactic fermentation: Genetics and Genetic Engineering, GIM90, 6th International Symposium on Genetics of Industrial Microorganisms, Strasbourg (1990)].

From a purified preparation of this malolactic enzyme, the Inventors obtained preparations of polyclonal antibodies specifically directed against this enzyme. A *Lactococcus lactis* DNA library was then prepared in the vector λgt11, in *E. coli*. The screening of this library with the antibodies obtained made it possible to clone DNA fragments, which represent between the whole lot 4.5 kb of the same region of genomic DNA of *Lactococcus lactis*, containing the malolactic gene, and a fragment of the gene for malate permease, these genes being organized into operon. The Inventors identified a 2684 bp DNA fragment including the entire gene for the malolactic enzyme, and determined the sequence of this fragment, which is represented in the sequence listing in the annex under the number SEQ.ID.NO.1. In addition, the expression of the malolactic gene has been obtained in various prokaryotic and eukaryotic hosts. Thus, the introduction of the *Lactococcus lactis* malolactic gene into *E. coli*, under the control of its own regulatory elements as well as the expression of the said gene in yeast under the control of yeast regulatory elements have been achieved.

The subject of the present invention is a nucleic acid fragment, characterized in that it comprises the sequence of the gene for the malolactic enzyme of *Lactococcus lactis*.

By "sequence of the gene for the malolactic enzyme of *Lactococcus lactis*", there is understood in particular the coding sequence stretching from nucleotides 466 to 2085 (inclusive) of the sequence SEQ. ID. NO 1 represented in the sequence listing in the annex, as well as any sequence which, taking into account the degeneracy of the genetic code, encodes the same polypeptide; this definition also comprises the sequences carrying minor modifications intended to permit a better expression of the gene in a determined host.

The invention also encompasses nucleic acid fragments comprising a sequence homologous or complementary to the sequence of the gene for the malolactic enzyme of *Lactococcus lactis*, as defined above, or to a fragment of at least 10-mer, preferably of at least 20-mer, of the said sequence, and which can be used in particular as probes for the location of the said gene and/or as primers for its amplification.

The subject of the invention is also expression cassettes, comprising the sequence of the gene for the malolactic enzyme of *Lactococcus lactis*, under the control of sequences capable of regulating the expression of the said gene.

By "sequences regulating the expression of a gene", there is understood sequences of the promoter and terminator type which are active in the host in which it is desired to obtain the expression of the said gene. The promoters and terminators of various genes can be used, associated in various combinations.

Among the sequences which can be used to obtain the expression, in yeast, of the gene for the malolactic enzyme of *Lactococcus lactis*, there may be mentioned, as non-limitative example, the promoters and terminators, known per se, of the genes for alcohol dehydrogenase I (ADHI), for phosphoglycerate kinase (PGK), and for glyceraldehyde-3-phosphate dehydrogenase (GAPDH).

The expression cassettes in accordance with the invention can be carried by plasmids, or integrated into the chromosomal DNA of the host yeast.

The subject of the invention is also recombinant vectors characterized in that they comprise at least one DNA fragment containing the sequence of the gene for the malolactic enzyme of *Lactococcus lactis*, as defined above.

According to a preferred embodiment of the present invention, the said vectors are expression vectors, comprising an expression cassette as defined above.

According to a preferred embodiment of the present invention, the said vectors comprise regulatory sequences which are active in the yeast.

Advantageously, the vectors in accordance with the invention are shuttle vectors, also possessing a bacterial replication origin and a selectable marker in a bacterium (for example, gene for resistance to an antibiotic).

These vectors can be selected on the basis of the nature and the strength of the regulatory elements which enter into the expression cassette. The promoters and terminators described above, or any other sequence which makes it possible to control and regulate the expression of a gene in yeast, can be chosen.

Another criterion for the choice of vectors lies in the number of copies thereof, which is determined by the choice of the replication origin.

By way of example, a choice can be made between the following vectors:

Replicative vector (YEp) at high copy number, possessing as replication origin in yeast, a portion of the endogenous 2 μ plasmid.

Replicative vector (YRp) at high copy number, possessing as replication origin, a chromosomal ARS sequence.

Linear replicative vector (YLp) at high copy number, possessing telomer sequences as replication origin.

Replicative vector (YCp) at low copy number, possessing a chromosomal ARS sequence and a centromere sequence.

Preferably, the vectors in accordance with the invention also contain selectable markers in yeast, such as markers for auxotrophy: $URA_3$, $LEU_2$, $HIS_3$, $TRP_1$, ADE, and the like and/or markers for resistance to antibiotics (G418, hygromycin B, chloramphenicol, phleomycin), to herbicides (sulphometuron-methyl), to copper, and the like.

Vectors in accordance with the invention, carrying the gene encoding the malolactic enzyme of *Lactococcus lactis* can be introduced into any yeast strain, by various transformation techniques.

Among the most common transformation techniques which can be used, there may be mentioned the protoplasts technique, the technique of permeabilization to lithium salts and electroporation.

In all cases, the process for this construction comprises the following steps:

construction of an expression cassette comprising the gene for the malolactic enzyme and the regulatory elements of variable strength;

introduction of this cassette either as single copy, or as multiple copies into the yeast, The choice can also be made to integrate the gene for the malolactic enzyme of *Lactococcus lactis*, equipped with its control sequences, into the genome of the yeast, in which case an integrative vector (YIp) possessing no replication origin in the yeast will be chosen for example; it is also possible to integrate this gene using other techniques, for example co-transformation.

It is possible to modulate the level of expression of the gene encoding the malolactic enzyme of *Lactococcus lactis*, by adjusting especially the number of copies of the gene which are introduced into the yeast, and/or the strength of the regulatory elements associated therewith.

The subject of the present invention is also strains of transformed eukaryotic or prokaryotic cells, characterized in that they contain at least one heterologous DNA fragment carrying at least one copy of a gene encoding the malolactic enzyme of *Lactococcus lactis*, under the control of sequences regulating the expression of the said gene in the said cell.

According to a preferred embodiment of the present invention, the said cells are yeast cells.

The yeast strains in accordance with the invention find numerous applications in the food industry and in particular in the field of oenology for carrying out malolactic fermentation.

According to a preferred arrangement of this embodiment, the said yeasts belong to the genus Sacharomyces.

According to another preferred arrangement of this embodiment, said yeasts belong to the genus Schizosaccharomyces.

Schizosaccharomyces is sometimes used in oenology for its capacity to degrade malate. However, its use is limited because this degradation which is carried out using the malic enzyme does not produce lactate, but ethanol and $CO_2$, which results in a substantial deacidification, which may have negative influences on the characteristics of the wine.

Strains of Schizosaccharomyces obtained in accordance with the invention and expressing the gene for the malolactic enzyme, carry out the malolactic fermentation with degradation of L-malate to L-lactate, and thus have the advantage of permitting a much less substantial deacidification than that which results from the malate/ethanol conversion.

These Schizosaccharomyces strains can have numerous uses in oenology; they can for example be used:

in co-culture with an oenological strain of *Saccharomyces cerevisiae*;

as immobilized cells.

BRIEF DESCRIPTION OF THE DRAWINGS

A more complete appreciation of the invention and many of he attendant advantages thereof will be readily obtained as the same becomes better understood by reference to the following detailed description when considered in connection with the accompanying drawings.

FIG. 2 shows the combination of a region of DNA coding for malolactic gene with oligonucleotide primer 1 or 12, respectively containing XhoI and BamHI sites, and with oligonucleotide primers 3 or 13, on the 3' side, respectively having XbaI and SacI sites;

Figure 1:
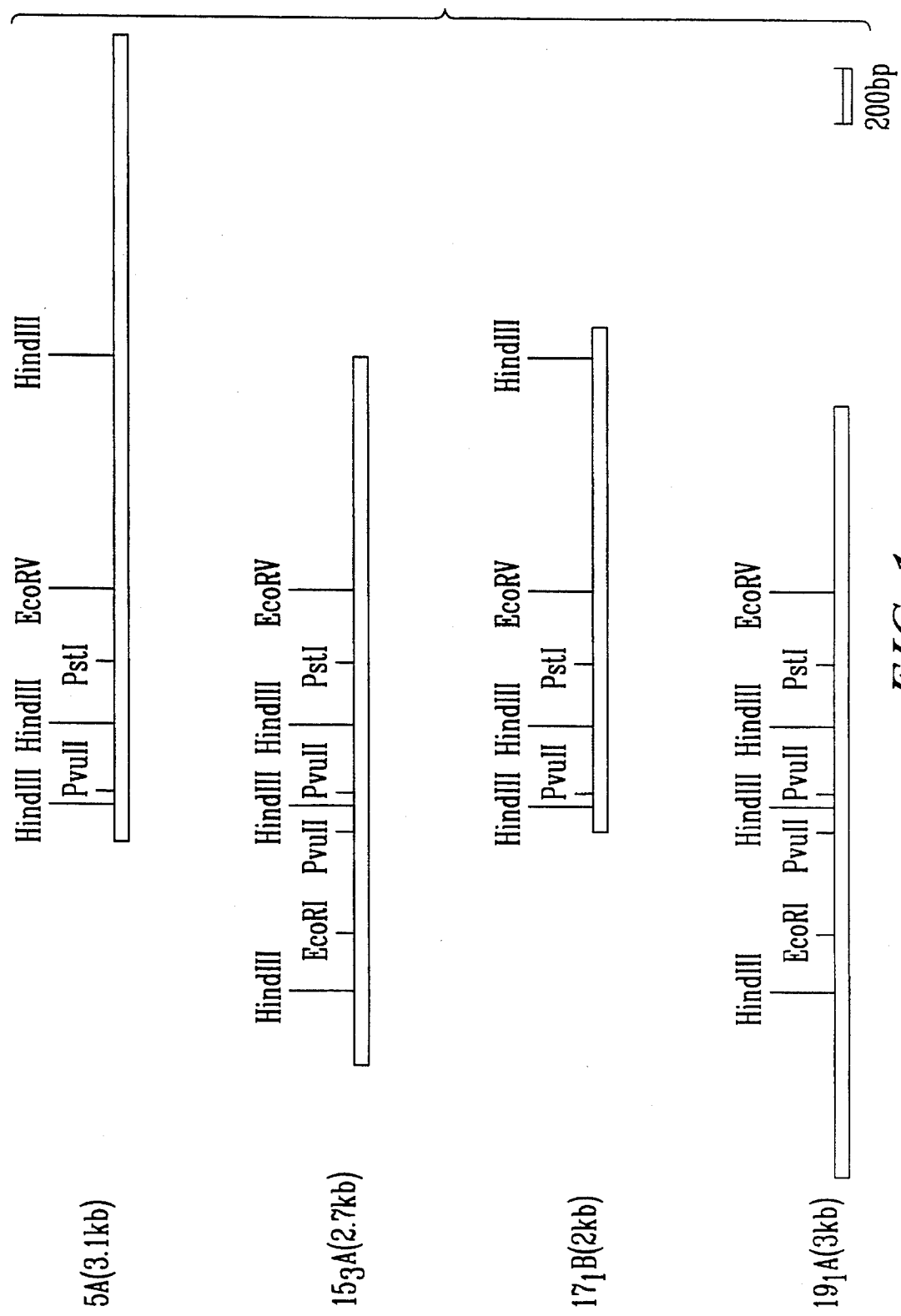
FIG. 1 shows the restriction maps of four of five DNA fragments of digested *Lactococcus lactis* DNA having a common region ligated into vector λgt11, with the inserts subcloned into plasmid pUC18.

The present invention will be understood more clearly with the aid of the additional description below, which refers to examples describing the cloning of the gene for the malolactic enzyme of *Lactococcusa lactis* and its expression in bacteria and yeasts.

General Methods

Malolactic enzyme was purified as described by RENAULT (1990, communication cited earlier); cf. also C. ROULLAND, (DEA in oenology-ampelography, September 1988, University of Bordeaux II).

The general techniques for manipulation of nucleic acids and molecular cloning to which reference is made in the examples below are those described by SAMBROOK et al. [Molecular Cloning: A Laboratory Manual (second edition), Cold Spring Harbor Laboratory Press, Cold Spring Harbor, N.Y. (1989)].

EXAMPLE 1

Purification of Malolactic Enzyme

The extraction procedure is briefly recalled below:

Strain—culture conditions

*Lactococcus lactis* (IL 1441) is cultured in the following medium:

| | | |
|---|---|---|
| Yeast extract | 6 | g |
| Tryptone | 2 | g |
| Glucose | 15 | g |
| DL-malic acid | 15 | g |
| $K_2HPO_4$ | 0.5 | g |
| $KH_2PO_4$ | 0.5 | g |
| $MgSO_4$ | 0.4 | g |
| NaCl | 0.02 | g |
| $FeSO_4$ | 0.004 | g |
| $MnSO_4$ | 0.02 | g |
| $H_2O$ | qs 1 | l |

The pH is adjusted to 5%. The sterile medium is inoculated with 10% (v/v) of a preculture.

Preparation of a Crude Extract and Assays

The cells are cultured in 3 liters of the above medium at 28° C., for 24 hours, harvested by centrifugation at 1000 g for 10 min at 4° C., and washed twice with 0.9% NaCl.

The pellet is taken up in 30 ml of phosphate buffer (0.1M, pH 6.0). The cells are ground by ultrasound for 6 min at 0° C. After centrifugation (30,000 g, 15 min, at 4° C.) the supernatant constitutes the crude extract.

The proteins are assayed by BCA Protein Assay Reagent (PIERCE).

The malolactic activity is measured by the decarboxylation of malic acid monitored using a $CO_2$ electrode (EISCHWEILER).

Purification of the Enzyme

After treatment with DNAse I (1 mg/ml and 15 min of incubation at room temperature), the crude extract is subjected to a fractional precipitation with ammonium sulphate (35% saturation, then 70%).

The supernatant from the precipitation at 70% has no activity. The pellet, taken up in 2 ml of 0.1M phosphate buffer, pH 6.0, and which contains all the malolactic activity, is deposited onto a filtration column on ACA 34 gel (ULTROGEL; fractionation range from 20,000 to 350,000) 40 cm in length and 2.6 cm in diameter, previously equilibrated with elution buffer: 0.01M phosphate buffer, pH 6.0, 0.1M KCl. The elution is performed with a flow rate of 18 ml/h. The volume of fractions collected is 2.4 ml.

Under these conditions, the most active fractions correspond to fractions 50 to 54. They are combined for an additional purification by isoelectric focusing. The isoelectric focusing is performed on a 110 ml LKB column. The pH gradient is formed by means of the ampholines used at 2% and is stabilized by a glycerol density gradient which is established during the filling of the column. The most active fraction which focuses at pH 4.3, the phi of the protein, is recovered and then undergoes an additional step of purification by ion-exchange chromatography (SEPHAROSE Q anion-exchange column, PHARMACIA).

The elution is performed by a gradient from 0 to 0.5M NaCl, in a 50 mM Tris-Hcl buffer, pH 7.6, 0.1 mM EDTA, 1 mM β-mercaptoethanol.

The fraction containing the malolactic activity is eluted at an NaCl concentration of 0.33M. It is this fraction which is used for the production of antibodies.

EXAMPLE 2

Production of Polyclonoal Antibodies Directed Against the Malolactic Enzyme of *Lactococcus Lactis*

The antibodies were obtained by injecting into two rabbits a portion of the purified preparation of malolactic protein according to the following procedure:

Subcutaneous injection of 2 ml of solution of malolactic protein (100 μg in 0.3M NaCl buffer) supplemented with 2 ml of complete Freund's adjuvant.

Second injection 40 days later, with the same quantity of malolactic protein and 2 ml of incomplete Freund's adjuvant.

The blood of the two rabbits is recovered 12 days after the 2nd injection, left for 24 h at 4° C. to allow coagulation, centrifuged at 10,000 g for 10 min at 4°, and the serum recovered is aliquoted and stored at −20° C.

The antibodies to malolactic enzyme were then tested by ELISA test carried out on both sera (called 120 and 119) obtained from rabbit serum according to the procedure described by SAMBROOK et al. [(1989)]. This analysis made it possible to determine that the optimal dilution for the use of the antibodies was 1/1000th.

The specificity of the antibodies was then determined by immunoelectrophoretic transfer (Western blotting).

The proteins from a crude extract of *Lactococcus lactis* (prepared as described in Example 1), on the one hand, and from the purified preparation of malolactic enzyme, on the other hand, were separated by SDS-PAGE electrophoresis and transferred onto nitrocellulose membrane.

The polyclonal antibodies obtained are then bound to the membrane and revealed by anti-rabbit antibodies coupled to alkaline phosphatase.

The serum 120 recognizes, on the crude extract and on the purified fraction, a predominant band of molecular weight of about 60 kD corresponding to the malolactic enzyme, and several contaminant bands of lower molecular weight.

On the other hand, the serum 119 recognizes on the purified fraction, as well as on the crude extract, a single band, corresponding to the malolactic enzyme; this highly specific serum was therefore used for the subsequent experiments.

EXAMPLE 3

Construction of a Library for Expresson of Genomic DNA of *Lactococcus Lactis* in *E. Coli* a) Extraction of *Lactococcus lactis* DNA

The *Lactococcus lactis* genomic DNA library was prepared in the vector λgt11.

The genomic DNA of *Lactococcus lactis* IL 1441 was, in a first stage, extracted and purified. For that, 500 ml of a culture in exponential phase are centrifuged at 5000 g for 10 min. The pellet is taken up in 5 ml of TE (10 mM Tris, 1 mM EDTA, pH 8) containing 150 mM NaCl and 1 mg/ml of lysozyme, and incubated for 10 min at 37° C. 1 ml of SDS, 25% in EDTA, 0.1M, pH 8, are added and the mixture is incubated for 15 min at 60° C. The DNA is purified by two extractions with phenol-chloroform, followed by two others with chloroform-isoamyl alcohol (24:1). A final purification is carried out on caesium chloride gradient in the presence of ethidium bromide. The ethidium bromide is extracted with isoamyl alcohol. After dilution with 2 volumes of water, the DNA is precipitated with 6 volumes of ethanol. The precipitate is recovered using a rod and dissolved in 1 ml of TE. The DNA concentration in solution was determined (1 μg/μl) by measurement of the OD at 260 nm.

b) Digestion of the *Lactococcus lactis* DNA

125 μg of *Lactococcus lactis* DNA are partially digested with two units of enzyme AluI and two units of HaeIII for 35 min at 37° C. so as to generate blunt ends. The digestion is stopped by addition of EDTA to 0.1M final.

The digested DNA is precipitated with 1/20 vol of 3M sodium acetate and 2 volumes of ethanol. After centrifugation, the DNA is taken up in 300 μl of TE and the fragments separated on sucrose gradient for 15 hours at 25,000 rpm.

Fractions of 0.5 ml are harvested and analysed on 0.8% agarose gel. The fraction containing fragments of 1.5 and 4 Kb is dialysed against TE for 4 hours.

c) Ligation of the digested DNA into the vector λgt11

The vector μgt11 (derived from bacteriophage λ) was chosen to prepare the expression library. The principle of the preparation of the library consists in inserting DNA fragments into the 3' region of the phage encoding the β-galactosidase gene, so as to express hybrid proteins under the control of the β-galactosidase promoter.

A kit for cloning into λgttII (AMERSHAM) was used according to the procedure recommended by the supplier.

1 μg of (blunt-ended) DNA digested and dialysed as described above was inserted into the vector λgt11 according to the following principle:

The DNA is ligated to dephosphorylated adaptors having a blunt end and another EcoRI cohesive end. After removal of the free adaptors by purification on exclusion column, the "adapted" DNA fragments are phosphorylated and ligated to the arms of the vector which were also digested with EcoR1 and dephosphorylated.

The in vitro packaging of the phage particles is then carried out. The library thus obtained was titrated by infection of the bacterial strain *E. coli* 1090 [hSd (r⁻km⁺k) lac U169, ProA⁺, lon⁻, araD139 StrA, SupF, trpC22: Tn10 (pMC9)] with an aliquot fraction of the phage suspension, and the transformants selected on LB medium (bactotryptone 10 g/l, yeast extract 5 g/l, NaCl 10 g/l)+ampicillin (50 μg/ml) at 43° C. (to induce bacterial lysis). The lysis plaques are obtained after 4 h of incubation.

The library thus obtained represents about 3 times the *Lactococcus lactis* genome.

EXAMPLE 4

Screening of the Genomic DNA Library a) Plating of the library and preparation of the filters 75,000 lysis plaques were obtained by plating the library on LB+ epicillin+MgCl$_2$ medium and incubation for 3 h 30 min at 43° C. (conditions for non-expression). The plates are covered with nitrocellulose filters (C extra, AMERSHAM), impregnated with 10 mM IPTG and incubated for 4 h at 37° C., so as to induce the expression.

The filters are rinsed in TNT (10 mM Tris-HCl, pH 8, 150 mM NaCl, 0.05% Tween 20), and then incubated with gentle stirring for 30 min at room temperature in the same buffer.

In order to limit the detection of "false positive" clones which can hybridise in a non-specific manner during the screening of the library, a second series of filters, constituting duplicates of the first series, were deposited on the plates, incubated and treated in the same manner.

b) Depletion of the serum 119

The immunological screening of the library is carried out with the aid of the serum 119 previously depleted against the *E. coli* proteins. The depletion of the serum is performed as follows:

A culture of *E. coli* Y1090 is carried out in 100 ml of LB+ampicillin for 24 h at 37° C. The culture is centrifuged at 5000 g for 10 min at 4° C. The pellet is taken up in 3 ml of buffer (50 mM Tris, 10 mM EDTA, pH 8), and the suspension frozen at −20° C. and thawed (several times). The cells are completely lysed by sonication at 0° C. (six times 20 seconds), then centrifuged at 12,000 g for 10 min at 4° C. The lysate is recovered and incubated for 4 h at room temperature in the presence of 1 ml of antibody 119 diluted 1/10th in TNT buffer+1% gelatin+3% BSA+5% powdered skim milk.

The depleted serum is stored at 4° C. in the presence of sodium azide (0.05%).

c) Immunological screening of the library

The nitrocellulose filters are then incubated in the presence of the depleted serum 119 as described above, and the revealing of the bound antibodies is carried out with the aid of anti-rabbit antibodies coupled to alkaline phosphatase, as previously described.

Only the clones showing a positive signal on the two filters are taken into consideration. 24 positive clones were thus selected.

In order to verify the specificity of the signal obtained, the positive clones were subcloned and a second detection with the aid of antibodies was carried out. Around each positive lysis plaque, an agarose carrot is removed and incubated in 500 μl of SM buffer (NaCl 6 g/l, MgSO$_4$ 7H$_2$O 2 gl, Tris base 6 g/l, gelatin 0.01%, pH 7.5), for 2 hours at 4° C. in order to allow diffusion of the phage particles. This suspension is again used to infect *E. coli* 1090 and the mixture plated on LB+ampicillin+MgCl$_2$ plate as above, so as to obtain well isolated lyses plaques. A second screening by the serum 119 carried out as above made it possible to eliminate 14 clones out of the 24 tested, which no longer exhibited significant signals. The other 10 clones, very clearly positive were selected.

d) Characterization of the recombinant clones

The phage DNA from the 10 positive clones was extracted and analysed. A well isolated positive lysis plaque (sub-clone) was systematically used as starting material.

The DNA is extracted from confluent lysis plaques on LB+ampicillin plates. The plates are covered with 5 ml of SM buffer and stirred at 4° C. for 2 hours. The suspension is recovered, supplemented with few drops of chloroform and centrifuged at 4000 g for 10 min at 4° C. in order to remove the bacterial debris. The DNA is extracted from the phage suspension thus purified.

The first analysis consisted in amplifying, by PCR, the inserts carried by the recombinant phages in order to determine their size.

Two oligonucleotides [leda gt11 Primer (forward) 24-MER and lambda gt11 Primer (reverse) 24-MER, company BIOLABS] corresponding to β-galactosidase sequences surrounding the EcoRI cloning site were used as primers for amplification of the inserts.

Analysis of the amplification products on agarose gel (1.6%) made it possible to determine that the 10 λgt11 clones selected had inserts of between 2 and 3.5 kb in size.

In order to establish the restriction map of the cloned DNA fragments, the inserts of the λgt11 vectors were subcloned into the plasmid pUC18 [YANISHPERRON et al. Gene No. 33, p. 103–119, (1985)]. It was thus possible to obtain the subcloning of 6 inserts.

The restriction map of the 6 inserts was prepared; 5 of the 6 inserts have a common region, suggesting that these 5 inserts come from the same genomic fragment. This was verified by Southern hybridization of restriction fragments of *Lactococcus lactis* genomic DNA separated on agarose gel and transferred onto Nylon membrane, with the inserts radioactively labelled with $^{32}$p.

The restriction maps of 4 of these 5 inserts are represented in FIG. 1.

The sizes of the inserts represented are 3 kb, 2.7 kb, 2 kb and 3 kb. As these inserts overlap, the total size of the cloned region is 4.5 kb.

The 6th clone, which has an insert having a restriction map without any similarity with that of the other 5 clones, comes from a different genomic DNA fragment.

In order to determine whether one of the two types of cloned DNA fragments contained the 5' region of the gene encoding the malolactic enzyme of *Lactococcus lactis*, a Southern hybridization of the inserts separated on agarose gel and transferred onto nylon membrane, with a probe of oligonucleotides derived from the protein sequence of the NH$_2$-terminal end of the malolactic enzyme (P. RENAULT, communication cited earlier) was carried out. The probe chosen is a mixture of oligonucleotides deduced from the sequence including the first 6 amino acids:

ATG(A,C)G(G,A,T,C)GC(G,A,T,C)CA(T,C)GA(G,A)AT (SEQ ID NO: 9)

The 5 inserts coming from the same DNA fragment hybridize with the probe; which proves that the 5' end of the gene encoding the malolactic enzyme of *Lactococcus lactis* is contained in the 5 cloned inserts. On the other hand, no hybridization was detected on the 6th clone.

e) Sequence of the clone P153A

The nucleotide sequence of one of the 5 clones P153A having a 2.7 kb insert was determined by dideoxy-termination method in an Applied Biosystem sequencer. The total sequence of the insert is represented in the annex, under the identification number SEQ ID NO 1, as well as the amino acid sequence which is deduced therefrom. The coding region of the malolactic gene is 1620 nucleotides. The first 20 amino acids deduced from the nucleotide sequence obtained are identical to the protein sequence determined from the purified enzyme, with the exception of the 14th amino acid (lysine instead of cysteine determined from the purified enzyme). This open reading frame is capable of encoding a protein of 53 kD, this is completely compatible with the size of the malolactic enzyme of *Lactococcus lactis* estimated by gel filtration and SDS-PAGE electrophoresis (about 60 kD).

The sequence SEQ ID NO 1 comprises, in addition, 465 nucleotides upstream of the codon for initiation of translation. This sequence comprises the entire promoter of the gene for the malolactic enzyme. The *Lactococcus lactis* promoters have a size of the order of 150 nucleotides upstream of the initiation codon. Furthermore, the signals characteristic of initiation of transcription of the *Lactococcus lactis* genes are present.

Downstream of the open reading frame, 596 nucleotides were sequenced, and another open reading frame of 581 nucleotides was detected in 3' of the malolactic gene in another reading frame.

The determination of homologies with the genes or known proteins was carried out by comparison of the nucleotide sequence SEQ ID NO 1, and the protein sequences deduced with databases.

As regards the open reading frame of 1620 nucleotides, very substantial amino acid and nucleotide conservations were detected with various malic enzymes, which are responsible for the decarboxylation of malate to pyruvate.

Moreover, a consensus sequence for binding of NAD was found.

These homologies are perfectly consistent with the function of the malolactic enzyme, which uses, as malic enzyme, malate as substrate, and requires NAD for the conversion of the substrate to lactate.

As regards the beginning of the reading frame identified downstream of the malolactic gene, amino acid homologies, which were also substantial (of the order of 40%), were identified with citrate permeases. It appears extremely probable that this open reading frame may correspond to the 5' region of a malate permease.

It therefore appears that the structural gene encoding the malolactic enzyme, and a portion of the malate permease gene are present on the DNA fragment sequenced, and that these genes are organized into operon.

EXAMPLE 5

Expression of the Malolactic Gene in *E. Coli*

The expression of the malolactic gene was studied in *E. coli*, in various transformants of the bacterial strain DH5α: p153A (clone sequenced), p5A, p191A (see restriction maps, FIG. 1).

The transformants as well as the control strain DH5α transformed with pUC18, were inoculated into a range of culture media at increasing malate concentration: 3 ml of M9 medium ($Na_2HPO_4$, $7H_2O$ 6 g/l, $KH_2PO_4$ 3 g/l, NaCl 0.5 g.l, $NH_4Cl$ 1 g/l, glucose 4 g/l), supplemented with thiamine 1 mg/l, aspartic acid 20 mg/l and ampicillin 20 mg/l, and containing 0; 0.3; 0.5 or 1% malate (w/v). The medium is buffered to pH 6.5 by the addition of citric acid.

The cultures were incubated at 37° C., with stirring, for 48 h.

As control, *Lactococcus lactis* was cultured in 8 ml of M9 medium containing 5 g/l of "YEAST EXTRACT" and the same malate range. The cultures were incubated at 28° C., for 48 h, under anaerobic conditions.

The cultures were then centrifuged for 10 min at 4000 g. The supernatants were recovered and tested for the presence of L-lactate. The L-lactate assay was performed with the aid of a kit (BOEHRINGER), according to the procedure described by the supplier.

The results, presented in Table I below (expressed in g/l) show a very clear production of lactate in the culture supernatant of the transformants p153A and p191A, whereas no trace of lactate is detected in the supernatant of the control strain (*E. coli* DH5 transformed with pUC18). Another transformant, p5A, which was tested under the same conditions, does not, on the other hand, produce lactate. This is explained by the fact that the malolactic gene carried by the recombinant vector p5A has a 3' end from which 200 nucleotides have been truncated. This region therefore seems to be essential for the malolactic activity.

In the absence of malate, there is no significant production of lactate in the culture supernatant of the transformants p153A and p191A, nor of the control strain transformed with pUC18. This is explained by the fact that *E. coli* does not produce L-lactate under these culture conditions.

In the presence of malate, no production of lactate is observed for the control strain. On the other hand, as regards the transformants p153A and p191A, a significant production of lactate is observed in the presence of 0.1, 0.3 and 1% malate.

The level of lactage produced is quite low when it is compared with that produced by the control strain *L. lactis* tested under the same conditions and starting with the same malate concentrations. However, it should be noted that the production of L-lactate in *L. lactis* corresponds to the L-lactate produced by malolactic fermentation, and also to a high proportion of the L-lactate produced by degradation of sugars, via L-LDH which converts pyruvate to lactate.

Moreover, it is difficult to determine the portion of malate which is really available for the malolactic fermentation. Indeed, under the culture conditions used for *E. coli*, a significant portion of the malate can be used via the tricarboxylic cycle.

TABLE I

| Bacterial strain | % malate in culture medium | | | |
|---|---|---|---|---|
| | 0 | 0.3 | 0.5 | 1 |
| *E. coli* DH5α (pUC18) | 0.001 | 0.017 | 0.008 | 0.015 |
| *E. coli* (p153A) | 0.015 | 0.12 | 0.23 | 0.31 |
| *E. coli* (p191A) | 0.017 | 0.17 | 0.15 | 0.2 |
| *Lactococcus lactis* | 2.6 | 5.09 | 8.5 | — |

EXAMPLE 6

Expression of the Malolactic Gene in Yeast

In order to carry out the expression of the malolactic gens cloned into yeast, the coding region was placed under the control of yeast regulatory elements (promoters and terminators), in yeast/*E. coli* shuttle vectors.

a) Introduction of the malolactic gens into the multicopy plasmid pVT10-U

The expression plasmid pVT100-U was used. This plasmid contains the replication origin of yeast 2 µ, the selectable marker URA3 and the strong ADH regulatory elements (alcohol dehydrogenase I promoter and terminator), as well as the bacterial elements (replication origin and the gens for resistance to ampicillin).

This plasmid has been described by VERNET et al [Gens 52; 225–233, (1987)].

The coding region of the malolactic gens was amplified by PCR starting with the plasmid p153A, with the aid of primers consisting of oligonucleotides derived from the sequence of the malolactic gene. In order to facilitate the cloning, the introduction of restriction sites XhoI upstream and XbaI downstream of the coding region was carried out during the amplifications.

The oligonucleotides used as primers are:

an oligonucleotide which makes it possible to isolate the coding region at the level of the codon for initiation of translation ATG (primer 1) and containing a XhoI site.

On the 3' side, the oligonucleotide chosen (primer 3') is located a few nucleotides downstream of the codon for termination of translation.

The sequences as well as the exact positions of the primers used are indicated in FIG. 2.

The amplification was carried out in the following manner:

| | |
|---|---|
| primer 1 | 4 µl (30 pmol) |
| primer 3 | 4 µl (30 pmol) |
| Taq buffer 10X | 10 µl |
| Taq polymerase (5 µ/µl) | 0.5 µl |
| dNTP 2 µM | 10 µl |
| $MgCl_2$ 25 mM | 6 µl |
| p153A | 4 µl (40 ng) |
| H2O | 62 µl |

Amplification conditions: 30 seconds at 94° C., 30 seconds at 40° C., 1 min at 72° C. for 30 cycles.

The size of the amplified fragments was checked by analysing an aliquot an agarose gel.

100 ng of the amplified fragments were digested with XhoI and XbaI and ligated to 50 ng of pVT100-U vector previously digested with XhoI and XbaI and dephosphorylated.

Figure 3:
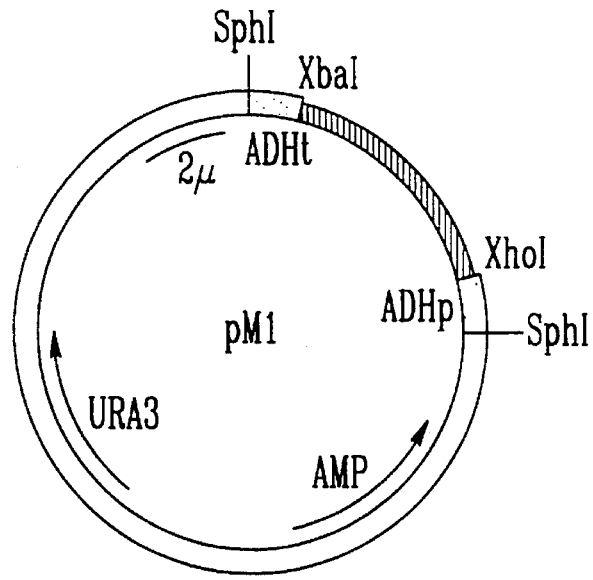
FIG. 3 is a restriction map of vector pM1 containing malolactic gene.

The vector pVT100-U obtained, called pM1, is represented in FIG. 3.

b) Transformation of the yeast

The yeast strain *Saccharomyces cerevisiae* SCV5M was transformed with the vector pM1.

The strain SCV5M was deposited on 18 June 1992 at the Collection Nationale de Cultures de Microorganismes, held by Institut Pasteur, under the number I-1222. It is a laboratory strain which is haploid, ura⁻, MATa, derived from an oenological strain.

The transformation method used is that of lithium acetate described by ITO et al. [J. Bacteriol. No. 153, pp. 163–168, (1983)].

c) Production of malolactic fermentation in yeast

Two of the transformants obtained, called ScV5M/pMIa and ScV5M/pMIb were tested for their capacity to carry out the malolactic fermentation (conversion of malate to lactate); these transformants were cultured under the following conditions:

- on the one hand, on minimum synthetic medium YNB (6.7 g/l "yeast nitrogen base without amino acid" (DIFCO), 20 g/l glucose) containing 0, 0.6 or 1% malate, buffered either to pH 3, or to pH 6 with citric acid (6.3 g/l).
- On the other hand, on synthetic medium mimicking the composition of a grape must, [SABLAYROLLES et BARRE, Sciences des Aliments, No. 6, p. 373–383 (1986)], buffered to pH 3.3.

The two media used do not contain uracil, which ensures a selection pressure for the plasmids.

A transformant of ScV5M by the plasmid pVT100-U containing no insert was used as negative control.

CULTURE AND ASSAY CONDITIONS 8 ml of medium are inoculated with the yeast strains (transformants and control). The growth is carried out in sterile tubes of 10 ml, at 28° C., for 60 h, without stirring.

The cultures are centrifuged for 5 min at 4000 g and the supernatant tested for the production of L-lactate using a Boehringer kit, as indicated in Example 5.

RESULTS

The results obtained are presented in Table II.

In the minimum synthetic medium YNB (Table II), in the absence as in the presence of malate (0.3 and 1%), no trace of L-lactate is detected with the control yeast (ScV5M/pVTU). This is completely consistent with the fact that *S. cerevisiae* is incapable of carrying out the conversion of malate to lactate, and that, on the other hand, under anaerobic conditions, it produces only traces of lactate from glucose, mainly in the form of D-lactate.

The transformed strains pM1a and pM1b, in the absence of malate, produce traces of L-lactate of the order of about fifty to about one hundred milligrams. It is probable that this slight production results from the conversion, by the malolactic enzyme, of a portion of the endogeneous yeast malate, metabolized from glucose. In the presence of malate in the culture medium (0.6 and 1% of malate), and in YNB media buffered to pH 3, or in synthetic broth (pH 3.3, 3 g/l of malate), a very significant production of L-lactate (from 0.5 to 0.7 g/l for the clone pMIa under these experimental conditions) is observed.

The highest production is observed in synthetic broth whose composition is very similar to that of the grape musts (0.7 g/l of L-lactate, equivalent to 7.7 µmol/ml).

Under the same culture conditions (YNB) but at pH 6, the production of L-lactate is very low, of the same order of magnitude as in the absence of malate. The difference in production of L-lactate according to the pH of the culture medium could be explained by a problem of permeation of the malate in *S. cerevisiae* at pH 6. At pH 3 or 3.3, a large portion of the malate (pK 3.5) present in non-dissociated form can enter inside the cell by mere diffusion. On the other hand, at pH 6, the malate, mainly in dissociated form, would enter less easily inside the cell.

The recombinant strains therefore degrade malate to lactate by malolactic fermentation, and with a higher efficiency at acidic pH, therefore under conditions similar to those in oenology.

TABLE II

ASSAY OF LACTATE IN *S. CEREVISIAE*

| Yeast strain | L-lactate produced (g/l) | L-lactate produced (µmol/ml) |
|---|---|---|
| ScVRM/pVT100-U in (pH = 3): | | |
| 0% malate | $2.4 \times 10^{-3}$ | 0.02 |
| 0.6% malate | $7 \times 10^{-3}$ | 0.07 |
| 1% malate | $9 \times 10^{-3}$ | 0.1 |
| in (pH = 6): | | |
| 0% malate | $3 \times 10^{-3}$ | 0.03 |
| 0.6% malate | $6 \times 10^{-3}$ | 0.06 |
| 1% malate | $10 \times 10^{-3}$ | 0.11 |
| Synthetic broth (pH = 3.3) | $9 \times 10^{-3}$ | 0.1 |
| ScV5M/pH1a in (pH = 3): | | |
| 0% malate | 0.15 | 1.66 |
| 0.6% malate | 0.4 | 4.4 |
| 1% malate | 0.52 | 5.7 |
| in (pH = 6): | | |
| 0% malate | 0.1 | 1.1 |
| 0.6% malate | 0.07 | 0.77 |
| 1% malate | 0.05 | 0.55 |
| Synthetic broth (pH = 3.3) | 0.7 | 7.7 |
| ScV5M/pM1b IN (Ph = 3): | | |
| 0% malate | 0.15 | 1.66 |
| 0.6% malate | 0.40 | 4.4 |
| 1% malate | 0.48 | 5.3 |
| in (pH = 6): | | |
| 0% malate | 0.11 | 1.22 |
| 0.6% malate | 0.08 | 0.88 |
| 1% malate | 0.056 | 0.62 |
| Synthetic broth (pH = 3.3) | 0.51 | 5.66 |

The same experiment was carried out on synthetic broth, and the production of lactate measured after culturing for 10 days; 1.5 g/l (equivalent to 17 µmol/ml) of lactate were produced under these conditions.

EXAMPLE 7

Expression of the Malolactic Gene in *Schizosaccharomyces Pombe*

The expression of the malolactic gene was also studied in *Schizosaccharomyces pombe*. For this purpose, the coding region of the malolactic gene was placed under the control of an *S. pombe* promoter, in an *S. pombe*/*E. coli* shuttle vector.

a) Introduction of the malolactic gene into the multicopy plasmid pART1

The expression plasmid pART1 was used. This plasmid contains the yeast replication origin ARS1, the selectable marker LEU2 and the *S. pombe* alcohol dehydrogenase promoter, as well as bacterial elements (replication origin and gene for resistance to ampicillin).

This plasmid has been described by McLeod et al., (EMBO J. 6; 729–736, 1987).

The coding region of the malolactic gene was amplified by PCR starting with the plasmid p153A, with the aid of primers consisting of oligonucleotides derived from the sequence of the malolactic gene. In order to facilitate the cloning, the introduction of BamHI restriction sites upstream and SaCI downstream of the coding region was carried out during the amplifications.

The oligonucleotides used as primers are:

an oligonucleotide which makes it possible to isolate the coding region at the level of the codon for initiation of translation ATG (primer 12) (SEQ ID NO: 4) and containing a BamHI site on the 3' side, the oligonucleotide chosen (primer 13) (SEQ ID NO: 6) is located a few nucleotides downstream of the codon for termination of translation and has a SacI site.

The sequences as well as the exact positions of the primers used are indicated in FIG. 2 (SEQ ID NO: 3–8).

The amplification was carried out in the following manner:

| primer 12 | 4 µl (20 pmol) |
|---|---|
| primer 13 | 4 µl (20 pmol) |
| Taq buffer 10X | 10 µl |
| Taq polymerase (5 U/µl) | 0.5 µl |
| dNTP 2 µM | 10 µl |
| mgCl2 25 mM | 6 µl |
| p153A | 10 µl (100 ng) |
| H2O | 65.5 µl |

Amplification conditions: 30 seconds at 94° C., seconds at 37° C., 1 min at 72° C. for 30 cycles.

The size of the amplified fragments was checked by analysing an aliquot on agarose gel.

100 ng of the amplified fragments were digested with BamHI and SacI and ligated to 50 ng of vector pART1 previously digested with BamHI and SacI and dephosphorylated.

Figure 4:
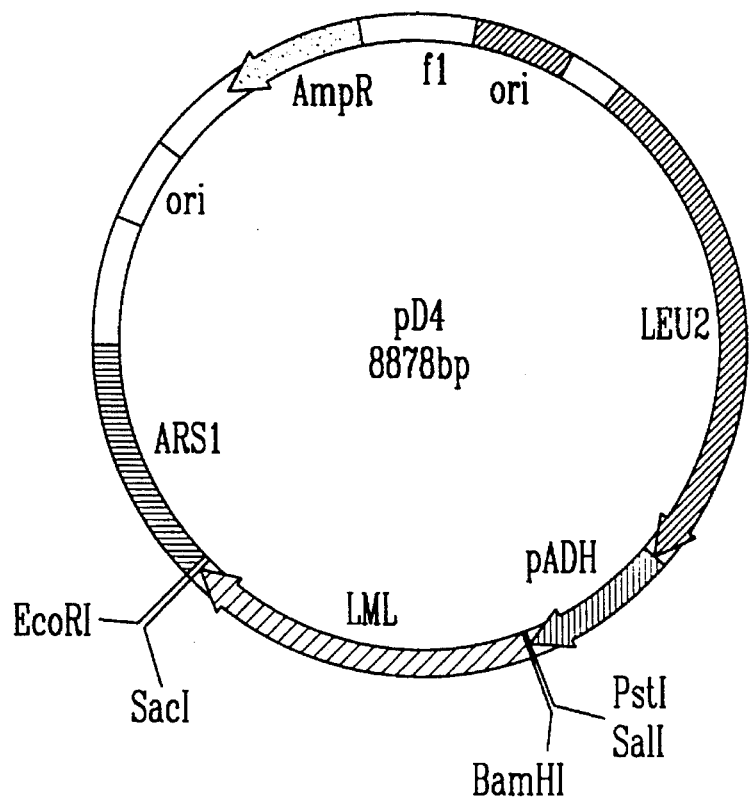
FIG. 4 is a restriction map of vector pD4 of an amplified DNA fragment containing malolactic gene with primer 12 (5' end) having a BamHI site and primer 13 (3' end) having a SacI site incorporated into vector pART1.

The vector obtained, called pD4, is represented in FIG. 4.

b) Transformation of *S. pombe*

An *S. pombe* strain auxotrophic for leucine was transformed with the vector pD4 and with the vector pART1. It is the laboratory strain leu1-32h+, which was supplied by J.KOHLI, Institute of General Microbiology, Raltzerstrasse 4, CH-3012, Bern, Switzerland.

The method of transformation used is that of transformation with lithium acetate adapted from Ito et al. (Journal of Bacteriology 153, 163–168, 1983).

c) Production of malolactic fermentation in *S. pombe*

One of the transformants obtained, called Sp/D42 was tested for its capacity to carry out the malolactic fermentation (conversion of malate to lactate). The transformant was cultured under the following conditions:

in minimum synthetic medium YNB containing 50 g/l of glucose and 5.5 g/l of L-malate, buffered either to pH 3.5 or to pH 6. This medium does not contain leucine, which ensures a selection pressure for the plasmids introduced.

A transformant of the same strain by the plasmid pART1 not containing insert was used as negative control.

8 ml of medium are inoculated with the yeast strains (transformant and control). The growth is carried out in sterile tubes of 10 ml, at 40° C., for one week, without stirring.

The cultures are centrifuged for 5 min at 4000 g and the supernatant tested for the production of L-lactate using a BOEHRINGER kit as indicated above. The degradation of L-malate was studied by assaying the L-malate residual in the culture medium with the aid of a BOEHRINGER kit.

The results obtained are presented in Table III below.

Under the various culture conditions tested, the control yeast Sp/pART1 produces only traces L-lactate (of the order of 20 to 40 mg/l). Indeed, like *S. cerevisiae*, *S. pombe* is incapable of converting malate to lactate, and, on the other hand, produces only traces of lactate under anaerobic conditions from glucose.

The strain transformed with the malolactic gene (Sp/D42), in the absence of malate, produces very low quantities of L-lactate, of the order of 170 to 300 mg/l. This slight production very probably results from the conversion, by the malolactic enzyme, of a portion of the yeast endogenous malate, metabolised from glucose. This was also observed with the *S. cerevisiae* transformants (Table II). In the presence of 5.5 g/l of L-malate in the culture medium, a very high production of L-lactate is observed for the transformant Sp/D42, from 2.4 to 3 g/l according to the pH of the culture medium. The highest production is observed at acidic pH, therefore under pH condition [sic] similar to those in oenology- The production obtained at pH 6 is also very high, compared to that obtained for the *S. cerevisiae* transformants at the same pH.

On the other hand, in the presence of 5.5 g/l of L-malate and at acidic pH, the transformant Sp/D42 is capable of degrading practically all the L-malate of the medium (at pH 3.5, only 150 mg/l of L-malate were not degraded) and furthermore, of converting more than 80% of the malate present to L-lactate (3.05 g/l).

TABLE III

ASSAY OF LACTATE IN *S. POMBE*

| Yeast strains | L-lactate produced (g/l) | Residual L-malate (g/l) |
|---|---|---|
| Sp/pART1 in (pH = 3.5) | | |
| 0% malate | not detected | |
| 0.55% malate | 0.04 | 1.4 |
| in (pH = 6) | | |
| 0% malate | 0.02 | |
| 0.55% malate | 0.03 | 4.6 |
| Sp/D42 in (pH = 3.5) | | |
| 0% malate | 0.17 | |
| 0.55% malate | 3.05 | 0.15 |
| in (pH = 6) | | |
| 0% malate | 0.3 | |
| 0.55% malate | 2.4 | 1.5 |

We claim:

1. An isolated nucleic acid fragment, which comprises a sequence of 1620 bp encoding the malolactic enzyme of *Lactococcus lactis*.

2. The nucleic acid fragment of claim 1, which comprises a sequence encoding the polypeptide SEQ. ID. NO. 2.

3. The nucleic acid fragment of claim 2, which comprises the nucleotides 466 to 2085 of the SEQ. ID. NO. 1.

4. An expression cassette, which comprises at least one DNA fragment of any one of claims 1–3, placed under the control of sequences for regulation of the expression of a gene.

5. The expression cassette according to claim 4, wherein the regulatory sequences are active in yeast.

6. A recombinant vector, which comprises at least one DNA fragment of any one of claims 1–3.

7. A recombinant vector which comprises an expression cassette of a DNA fragment comprising a sequence of 1620 bp encoding the malolactic enzyme of *Lactococcus lactis*, placed under the control of sequences for regulation of the expression of a gene.

8. A recombinant vector, which comprises an expression cassette of a DNA fragment comprising a sequence encoding the polypeptide SEQ. ID. NO. 2, placed under the control of sequences for regulation of the expression of a gene.

9. A recombinant vector, which comprises an expression cassette of a DNA fragment comprising nucleotides 466 to 2085 of the SEQ. ID. NO. 1, placed under the control of sequences for regulation of the expression of a gene.

10. A transformed eukaryotic or prokaryotic cell, which comprises at least one expression cassette of claim 4.

11. A transformed eukaryotic or prokaryotic cell, which comprises at least one expression cassette of claim 5.

12. The transformed cell of claim 10, which is a yeast cell.

13. The yeast cell of claim 12, wherein said yeast belongs to the genus Saccharomyces.

14. The yeast cell of claim 12, wherein said yeast belongs to the genus Schizosaccharomyces.

15. A process of performing malolactic fermentation, comprising:
    culturing a yeast cell of claim 12 in a medium comprising L-malate.

\* \* \* \* \*